United States Patent [19]

Goetz et al.

[11] 4,355,180
[45] Oct. 19, 1982

[54] PREPARATION OF PRIMARY AROMATIC AMINES FROM CYCLIC ALCOHOLS AND/OR KETONES

[75] Inventors: Norbert Goetz, Worms; Leopold Hupfer, Friedelsheim; Werner Hoffmann, Neuhofen; Manfred Baumann, Mannheim, all of Fed. Rep. of Germany

[73] Assignee: BASF Aktiengesellschaft, Fed. Rep. of Germany

[21] Appl. No.: 305,908

[22] Filed: Sep. 25, 1981

[30] Foreign Application Priority Data

Oct. 16, 1980 [DE] Fed. Rep. of Germany ....... 3039085

[51] Int. Cl.$^3$ ...................... C07C 85/08; C07C 85/02; C07C 85/18
[52] U.S. Cl. .................................... 564/398; 564/396; 564/402
[58] Field of Search ....................... 564/402, 398, 396; 252/473

[56] References Cited

U.S. PATENT DOCUMENTS

| | | | |
|---|---|---|---|
| 3,219,702 | 11/1965 | Van Verth et al. | 260/571 |
| 3,219,703 | 11/1965 | Kilbourne et al. | 564/398 |
| 3,219,704 | 11/1965 | Wilder et al. | 260/576 |
| 3,347,921 | 10/1967 | Carrubba et al. | 260/581 |
| 3,442,950 | 5/1969 | Barker et al. | 260/576 |
| 3,553,268 | 1/1971 | Solomon et al. | 260/581 |
| 3,931,298 | 1/1976 | Wollensak | 260/581 |
| 3,960,962 | 6/1976 | Shubkin | 260/581 |

FOREIGN PATENT DOCUMENTS

| | | | |
|---|---|---|---|
| 342662 | 7/1929 | United Kingdom | 564/402 |
| 1295672 | 11/1972 | United Kingdom | 564/398 |
| 1344574 | 1/1974 | United Kingdom | 564/402 |

*Primary Examiner*—John Doll
*Attorney, Agent, or Firm*—Keil & Witherspoon

[57] ABSTRACT

Aromatic amines, in particular substituted amines, are obtained from corresponding alicyclic alcohols or ketones, in one step, by amination and dehydrogenation with ammonia in the presence of hydrogen and of a palladium catalyst which also contains zinc or cadmium.

8 Claims, No Drawings

PREPARATION OF PRIMARY AROMATIC AMINES FROM CYCLIC ALCOHOLS AND/OR KETONES

The oldest, and currently still the most important, method of preparation of primary aromatic amines is the reduction of aromatic nitro compounds (Houben-Weyl, Methoden der organischen Chemie, 4th edition, volume 11/1, page 360 et seq.). It is a disadvantage that the preliminary nitration is relatively unselective in the case of substituted aromatics, and accordingly product mixtures are often obtained.

A possible way of arriving at individual primary aromatic amines is to react ammonia with cycloaliphatic (alicyclic) compounds having a suitable pattern of substitution, for example derivatives of cyclohexanol, cyclohexenol, cyclohexenone or cyclohexanone, to give the correspondingly substituted anilines, the reaction being visualized as proceeding through the hydroxyl group first being converted, by aminolysis, to an amino group (or the carbonyl group first being similarly converted to an imino group), after which an aromatic ring is formed by dehydrogenation of the cyclohexane ring. A discussion of the subject is to be found in Houben-Weyl, loc. cit., pages 126 et seq. and 611 et seq., and in Houben-Weyl, volume 4/2, page 338 et seq. (cf. also U.S. Pat. No. 3,553,268).

U.S. Pat. Nos. 3,219,702 and 3,219,704 describe the synthesis of aromatic amines from alicyclic ketones and ammonia or primary or secondary amines, in the presence of dehydrogenation catalysts. However, these processes have the disadvantage that in some cases hydrogen acceptors are required (U.S. Pat. No. 3,219,702), and that numerous by-products, for example cyclohexylamines, N-cyclohexyl-anilines or dicyclohexylamines, are formed.

U.S. Pat. No. 3,553,268 describes the preparation of aniline from a mixture of cyclohexanol, cyclohexanone and ammonia in the presence of a nickel catalyst. Allegedly, a high yield is achieved, but the process appears not to be applicable to substituted products and is furthermore restricted by the fact that only mixtures containing at most 65% of cyclohexanol can be used. Moreover, such a process is of relatively little interest specifically for the preparation of aniline, since it is well known that aniline can be most cheaply obtained from nitrobenzene.

U.S. Pat. Nos. 3,442,950 and 3,347,921 are also concerned with the reaction of a mixture of cyclohexanol and cyclohexanone and ammonia or primary amines over dehydrogenation catalysts. In these processes, problems are caused by relatively high-boiling products and other by-products, inter alia Schiff bases of aniline and cyclohexylamine, phenol, diphenylamine and phenylcyclohexylamine, so that its implementation would require a complicated procedure.

The fact that, for example, the reaction of a mixture of phenols and cyclohexanone derivatives (the latter being intended to serve as catalysts) with ammonia has already been proposed for the preparation of aromatic amines (cf. U.S. Pat. Nos. 3,960,962 and 3,931,298, and German Laid-Open Application DOS 2,208,827) shows that there is a need for an industrially feasible method of synthesis of aromatic amines.

It is an object of the present invention to provide a process whereby individual, preferably substituted, aromatic amines may be obtained from corresponding cyclic alcohols and/or ketones with the aid of ammonia, with or without hydrogen, and with the aid of a hydrogenating/dehydrogenating catalyst. More particularly, it is an object of the present invention to provide a catalyst suitable for the reaction of cyclohexanols, cyclohexanones and their mixtures.

We have found that this object is achieved by using a palladium catalyst which is supported on a carrier and which furthermore contains zinc and/or cadmium.

Using the invention it is possible to obtain, for example, amines of the general formula (I)

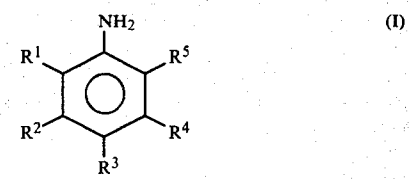

where $R^1$ to $R^5$ are each hydrogen or identical or different substituents, or some of these conjointly denote one substituent. Examples of the substituents are aliphatic groups of 1 to 20 carbon atoms, cycloaliphatic groups of 5 to 20 carbon atoms, aryl groups of 6 to 20 carbon atoms and aralkyl or alkylaryl groups of 7 to 20 carbon atoms. These groups may or may not contain oxygen and/or nitrogen as hetero-atoms, and two radicals can conjointly form a substituent by being joined by a molecular bridge. Accordingly, the starting materials can be defined as cyclic alcohols or ketones of the general formula II or IIa

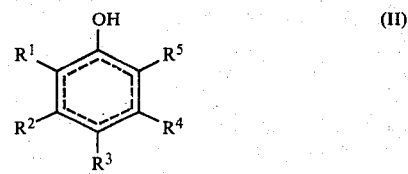

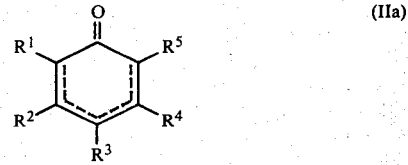

where $R^1$ to $R^5$ have the corresponding meanings. The central ring structure can be saturated or olefinically unsaturated; the position of the one or two double bonds is immaterial, as is indicated by the broken lines in (II) and (IIa).

It is surprising that the process according to the invention cannot be operated satisfactorily with palladium alone, and instead catalysts which are sufficiently selective for the desired aromatic amines to be obtained in high yield and excellent purity are only obtained by using additives in the catalyst; this is all the more astonishing since it had to be expected that the starting materials (cf. U.S. Pat. No. 3,347,792) might react in diverse ways. Dehydrogenation to a corresponding phenol, reaction with aromatic amines already formed, or with the imine intermediates, to give cyclohexylamines, formation of Schiff bases and hydrogenation to secondary amines would be only some of the possible sources of by-products. The different effects which catalysts of different composition have on the course of the reaction can easily be demonstrated by comparative experiments with the frequently recommended Raney nickel and normal palladium catalysts; a typical example of how the reaction proceeds over a conventional palladium catalyst is the Comparative Experiment apertaining to Example 14.

It is visualized that in the process according to the invention the adduct formation with ammonia takes place relatively rapidly and substantially completely, before the energetically equally favored direct dehydrogenation of the hexanol or ketone commences, so that the reaction results in the aromatic amine and not in the phenol.

Evidently, hydrogenation of the desired products, or of the intermediate cyclohexylamines, to bicyclic compounds also does not take place with the catalysts according to the invention, under the reaction conditions employed.

The cyclic alcohols required as starting materials can be obtained in a simple manner by hydrogenating phenols or cyclohexanones. The ketones can be obtained, for example, by reacting other ketones with α,β-unsaturated aldehydes or with identical or different ketones (Houben-Weyl, loc. cit., volume 7/2b, pages 1.629–1,634 and volume 8, pages 595–597; Org. Reactions 10 (1959), 179–555). Saturated cyclic ketones can be prepared by partial hydrogenation of unsaturated ketones (cf. Example 12). Finally, technical mixtures of cyclohexanols and cyclohexanones can be used; these can be of any composition and include, for example, the mixtures obtained by oxidizing cyclohexanones with oxygen.

Examples of cyclic ketones suitable for the process according to the invention are cyclohexanone, 2-methylcyclohexanone, 3-methylcyclohexanone, 4-methylcyclohexanone, cyclohex-2-en-1-one, 2-methylcyclohex-2-en-1-one, 3-methyl-cyclohex-2-en-1-one, 4-methyl-cyclohex-2-en-1-one, 2,6-dimethylcyclohexanone, 2,6-dimethylcyclohex-2-en-1-one, 3,5-dimethylcyclohexanone, 3,4-dimethylcyclohexanone, 2,3,6-trimethyl-cyclohex-2-en-1-one, 2,6-diisopropylcyclohexanone, 2-methyl-6-ethyl-cyclohexanone, 2-methyl-6-ethyl-cyclohex-2-en-1-one, 2-methyl-6-butylcyclohexanone, 2-dodecylcyclohexanone, 2-methyl-6-cyclohexyl-cyclohexanone, 2,6-dimethyl-3-phenyl-cyclohex-5-en-1-one, 2,6-dimethyl-3-(p-methylphenyl)-cyclohex-5-en-1-one, 2,6-dimethyl-3-(p-methoxyphenyl)-cyclohex-5-en-1-one, 2-methyltetralone (2-methyl-2-H-3,4-dihydro-naphthalen-1-one) and tetralone.

Examples of suitable cyclic alcohols are cyclohexanol, 2-methylcyclohexanol, 3-methylcyclohexanol, 4-methylcyclohexanol, 2,6-dimethylcyclohexanol, 3,5-dimethylcyclohexanol, 3,4-dimethylcyclohexanol, 2,3-dimethylcyclohexanol, 2,3,6-trimethylcyclohexanol, 2,4,6-trimethylcyclohexanol, 2,6-diethylcyclohexanol, 2,6-diisopropylcyclohexanol, 2,6-di-sec.-butylcyclohexanol, 2-tert.-butylcyclohexanol, 2-methyl-6-ethyl-cyclohexanol, 2-methyl-6-isopropyl-cyclohexanol, 2-methyl-6-sec.-butyl-cyclohexanol, 2-dodecylcyclohexanol, 2-methyl-6-cyclohexanol, 2,6-dimethyl-3-phenyl-cyclohexanol, 2,6-dimethyl-3-(p-methylphenyl)-cyclohexanol, 2,6-dimethyl-3-(p-methoxyphenyl)-cyclohexanol and 2-methyl-1,2,3,4-tetrahydro-naphth-1-ol.

The ammonia required for the reaction can be employed in stoichiometric amount or in any desired excess, relative to the ketone. In continuous operation, it has proved advantageous to pass hydrogen, conjointly with the ammonia, over the catalyst. The ratio of ammonia to hydrogen is, for example, from 1,000:1 to 10:1, ie. stoichiometric amounts of hydrogen are not necessary from the point of view of the outcome of the experiment. However, it has been found that in experiments continued for a long period the catalyst has a longer life if a certain excess of hydrogen, for example up to a 10-fold molar excess over ammonia, is used. If, for example, this ratio of hydrogen to ammonia is employed in the examples which follow, the result in respect of conversion and yield or selectivity remains substantially unchanged (in particular, no substantial amounts of hydrogenation products are formed), but the catalyst life in continuous operation is noticeably increased.

The reaction can be carried out either continuously or batchwise, in the gas phase or liquid phase. Where sufficiently easily vaporizable starting materials or mixtures are being reacted, continuous operation in the gas phase is preferred. The reaction can be carried out under atmospheric pressure or under pressures of up to 300 bar. Suitable reaction temperatures are from 100° to 350° C., especially from 150° to 300° C. Below 200° C., incomplete conversion is observed in some cases, especially with cyclohexanols, since the dehydration of the amines proceeds better at higher temperatures.

If olefinically unsaturated compounds are used as the starting materials, the reaction can also be carried out in two steps over the same catalyst, by first solely carrying out the hydrogenation, in the absence of ammonia (compare Example 12), and then converting the hydrogenated product in the manner according to the invention.

The liquid phase reaction can be carried out without a solvent or in the presence of solvents which are inert under the reaction conditions. Examples of suitable solvents are methanol, ethanol, n-butanol, tetrahydrofuran, dioxane, anisole, cyclohexyl methyl ether, 1,2-dimethoxyethane, toluene, xylene and cyclohexane. It is also possible to use an excess of the amine formed, ie. to recycle the reaction mixture; in that case, it is advisable to use an excess of ammonia.

When reacting olefinically unsaturated ketones (cyclohexenone derivatives) by the process according to the invention, it is advisable to carry out the reaction in the presence of a base, for example a tertiary amine or, preferably, in a tert.-amine as the solvent, since this suppresses the dehydrogenation of the ketones to the corresponding phenols (Examples 4 and 7). Examples of suitable tertiary amines are triethylamine, tri-n-propylamine, tri-n-butylamine, N,N-dimethyl-cyclohexylamine, N-methylpiperidine, N-ethylpiperidine, N-methylmorpholine and N-methylpyrrolidine. These compounds are employed either in a minor amount or, if they serve as the solvent, in a weight ratio, to the ketone, of up to 10:1.

The catalyst system used in the process of the invention contains, on the one hand, palladium, and, on the other hand, zinc alone or cadmium alone or, preferably, a mixture of both. The constituents of the catalyst are applied to a carrier, which may, for example, consist of alumina, silica, aluminum silicate, magnesium silicate, aluminum, chromium or iron spinels, or active charcoal. The use of alumina is preferred. The additives which impart the particular properties to the catalyst can be on the surface of the catalyst or form, on subsequent heating, a conjoint crystal lattice with the original carrier; an example of this is the formation of typical spinel lattices with zinc in the case of alumina carriers. This means that the carrier has an advantageous effect on the activity and life of the catalyst.

The additives can be applied, conjointly with palladium, by impregnating the carrier with a solution of, for example, their nitrates, chlorides, formates or oxylates. Subsequent heating, usually at from 400° to 600° C., gives an oxide mixture. If, in the case of an alumina carrier, spinel formation is to be achieved, for example with zinc, heating at from 900° to 1,300° C. is needed after impregnation (cf. Ullmanns Encyklopädie der technischen Chemie, 3rd edition (1955), volume 6, pages 242–244; Gmelin, System No. 35, Al, Tl 1934–1935, pages 26–28), the palladium being applied subsequently, in a conventional manner. The valency which zinc and cadmium assume on the catalyst is therefore also immaterial.

The palladium content of the catalyst is not critical and can be varied within wide limits. Advantageously it is from 0.05 to 15% by weight, based on the carrier. Zinc and cadmium are used in total amounts of, for example, from 0.01 to 5% by weight, based on the carrier. The weight ratio of zinc and cadmium to palladium can accordingly be, for example, from 10,000:1 to 1:1,500, preferably from 100:1 to 1:50. The catalyst is used in a conventional manner, for instance in the form of extrudates which can, for example, have a diameter of from about 3 to 5 mm and a length of 10 mm, or in the form of a powder. The form used depends, in the usual way, on the envisaged process technology.

In practice, it is possible to proceed, for example, as follows: palladium, together with the additional element (zinc and/or cadmium), is applied in the desired amount to γ-alumina (in extrudate or powder form) by impregnating with, for example, the appropriate aqueous nitrate solution or formate solution, and the material is then dried at 150° C., heated for 6 hours at 550° C. and reduced in a stream of hydrogen at 180° C. If it is intended to produce a catalyst having a spinel structure, initially only zinc and/or cadmium is applied to α-alumina by impregnation, and the material is then heated for 6 hours at 1,050° C. Thereafter, the carrier obtained is impregnated with aqueous palladium nitrate solution, and the material is reduced by heating in a stream of hydrogen at 180° C. If palladium-(II) chloride solution is used for the impregnation, reduction can be effected with an alkaline formaldehyde solution or with 5% strength aqueous hydrazine solution.

It should be noted that palladium catalysts which contain zinc and/or cadmium are already known, but have hitherto been used for other purposes, for example for special hydrogenations. Such catalysts are disclosed, for example, in German Pat. No. 1,115,238, German Laid-Open Application DOS 2,139,574 and German Published Application DAS 2,431,929.

The compounds prepared by the process of the invention are useful as, for example, intermediates for active ingredients of crop protection agents (German Published Application DAS 2,305,595, and German Laid-Open Applications DOS 2,648,008, DOS 2,513,732 and DOS 2,515,091).

In the Examples which follow, parts are by weight and bear the same relation to parts by volume as that of the kilogram to the liter.

EXAMPLE 1

A catalyst in extrudate form, containing 0.5% by weight of Pd, 0.11% by weight of Zn and 0.1% by weight of Cd on $Al_2O_3$ as the carrier is introduced into a tubular reactor having a capacity of one liter, corresponding to 1,000 parts by volume, and is brought to 210° C. Per hour, a gaseous mixture of 400,000 parts by volume of ammonia and 10,000 parts by volume of hydrogen, and, in co-current therewith, 100 parts of 2,6-dimethylcyclohexan-1-one in gaseous form, is passed over the catalyst bed at atmospheric pressure. The reaction product is cooled sufficiently to liquefy the high-boiling constituents, which can then be distilled, whilst the gaseous constituents are recycled. In this way, 100 parts of 2,6-dimethylcyclohexan-1-one give 92 parts of 2,6-dimethylaniline (xylidine) (boiling point 216° C. at atmospheric pressure), corresponding to a yield of 96% of theory.

EXAMPLE 2

Following the procedure as described in Example 1, 100 parts of 2,3,6-trimethylcyclohexan-1-one are reacted per hour, at 230° C. but otherwise under the same conditions as those of Example 1. 2,3,6-Trimethylaniline, boiling point 119° C./20 mm Hg, is obtained in a yield of 93%.

EXAMPLE 3

The procedure followed is as described in Example 1, but using tetralone as the starting material. α-Naphthylamine, of melting point 49° C., is obtained in a yield of 95%.

EXAMPLE 4

1,000 parts by volume of catalyst are introduced into a fluidised bed reactor, having a capacity of 1.3 liters or 1,300 parts by volume. The catalyst consists of 0.5% by weight of Pd, 0.11% by weight of Zn and 0.1% by weight of Cd on $Al_2O_3$ and has a particle size of from 0.2 to 0.6 mm. The reactor is set to 230° C. and, per hour, a correspondingly preheated mixture of 200,000 parts by volume of ammonia and 10,000 parts by volume of hydrogen is passed in. Per hour, a solution of 50 parts of 2,3,6-trimethylcyclohex-5-en-1-one in 50 parts of N-methylpiperidine is sprayed continuously into the fluidised catalyst bed produced by the gas stream. The reaction product is isolated by cooling the exit gases, and is distilled. 100 parts of 2,3,6-trimethyl-cyclohex-5-en-1-one give 89 parts of 2,3,6-trimethylaniline; yield: 91%.

EXAMPLE 5

The procedure followed is as described in Example 4, but using 3-methyl-cyclohex-2-en-1-one as the starting material. m-Toluidine, boiling point 203° C., is obtained as the end product, in a yield of 93%.

EXAMPLE 6

The procedure followed is as described in Example 4, but employing cyclohex-2-en-1-one as the ketone reactant. Aniline, boiling point 184° C., is obtained as the reaction product, in a yield of 88%.

EXAMPLE 7

In a stirred autoclave having a useful capacity of 300 parts by volume, a solution of 35 parts of 2,3,6-trimethylcyclohex-5-en-1-one in 35 parts of N-methylmorpholine, 34 parts of ammonia and 5 parts of a finely divided catalyst, containing 0.5% by weight of Pd and 0.1% by weight of Zn on $Al_2O_3$, are kept for 10 hours at 230° C. and the autogenous pressure (about 150 bar).

The mixture is then allowed to cool, filtered and purified by distillation. 18.2 parts of 2,3,6-trimethylaniline and 15.3 parts of 2,3,6-trimethylcyclohexan-1-one are obtained, the latter presumably through partial hydrogenation of the 2,3,6-trimethylcyclohex-5-en-1-one starting material with the hydrogen formed during the reaction. Since 2,3,6-trimethylcyclohexan-1-one can in turn be converted to the desired 2,3,6-trimethylaniline, for example as described in Example 1 or 2, the selectivity of the reaction is 96%.

(a) COMPARATIVE EXPERIMENT TO ACCOMPANY EXAMPLE 7

Following the method of Example 7, a solution of 35 parts of 2,3,6-trimethylcyclohex-5-en-1-one in 35 parts of N-methylmorpholine, 34 parts of ammonia and 5 parts of Raney nickel are heated for 10 hours in a stirred autoclave, of useful capacity 300 parts by volume, at 230° C. and under the autogenous pressure (about 150 bar). The mixture is then cooled and filtered, and the solvent is distilled off. According to analysis by gas chromatography, the reaction product contains 11% by weight of 2,3,6-trimethylaniline and 89% by weight of a mixture of starting material, 2,3,6-trimethylcyclohexan-1-one, 2,3,6-trimethylcyclohexanol and 2,3,6-trimethylcyclohexylamine, which cannot be separated by distillation.

(b) COMPARATIVE EXPERIMENT TO ACCOMPANY EXAMPLE 7

The procedure described above is followed, but instead of Raney nickel a catalyst containing 10% by weight of palladium on active charcoal is used. This experiment gives a product which, according to analysis by gas chromatography, consists of 38% by weight of trimethylaniline and 62% by weight of a mixture of starting material, 2,3,6-trimethylcyclohexan-1-one, 2,3,6-trimethylcyclohexanol and 2,3,6-trimethylcyclohexylamine, which cannot be separated by distillation.

EXAMPLE 8

The procedure followed is as described in Example 7, but using 2,6-dimethyl-3-phenyl-cyclohex-5-en-1-one as the starting material. 2,6-Dimethyl-3-phenylaniline, of boiling point 121° C./0.15 mm Hg, is obtained with a selectivity of 95%.

EXAMPLE 9

The procedure followed is as described in Example 7, but using 2,6-dimethyl-3-(p-methylphenyl)-cyclohex-5-en-1-one as the starting material. 2,6-Dimethyl-3-(p-methylphenyl)-aniline, of boiling point 132° C./0.2 mm Hg, is obtained with a selectivity of 87%.

EXAMPLE 10

The procedure followed is as described in Example 7, but using 2,6-dimethyl-3-(p-methoxyphenyl)-cyclohex-5-en-1-one as the starting material. 2,6-Dimethyl-3-(p-methoxyphenyl)-aniline, of boiling point 151° C./0.3 mm Hg, is obtained with a selectivity of 87%.

EXAMPLE 11

The procedure followed is as described in Example 7, but using 2-ethyl-cyclohex-5-en-1-one as the starting material. 2-Ethylaniline, of boiling point 209° C. at atmospheric pressure, is obtained with a selectivity of 93%.

EXAMPLE 12

(Example of partial hydrogenation of an olefinically unsaturated ketone)

In a stirred autoclave having a useful capacity of 5 liters, corresponding to 5,000 parts by volume, a mixture of 2,500 parts of 2,3,6-trimethylcyclohex-5-en-1-one and 250 parts of catalyst, which contains 0.5% by weight of Pd and 0.1% by weight of Zn on $Al_2O_3$, is hydrogenated under 20 bar hydrogen pressure, initially at 70° C. and then at 100° C., until the pressure remains constant. The liquid reaction mixture is filtered, giving 2,440 parts of filtrate which contains 96% of 2,3,6-trimethylcyclohexan-1-one and can be employed direct for the preparation of 2,3,6-trimethylaniline (for instance as described in Example 1).

EXAMPLE 13

A catalyst which is in the form of extrudate of 3 mm diameter and 10 mm length and which contains 1.8% by weight of palladium on a zinc-aluminum spinel as the carrier is introduced into a reactor consisting of a pressure-resistant cylindrical tube of 1.2 liters volume, and is heated to 220° C. Per hour, a gaseous mixture of 200 liters (S.T.P.) of ammonia and 200 liters (S.T.P.) of hydrogen and 100 g of vaporized 2,6-dimethylcyclohexan-1-one are passed over this catalyst bed under atmospheric pressure. The reaction product is cooled as soon as it leaves the reactor, and is distilled. 100 g of 2,6-dimethylcyclohexan-1-one give 93 g of 2,6-dimethylaniline of boiling point 216° C. at atmospheric pressure, corresponding to a yield of 97% of theory.

EXAMPLE 14

A catalyst which is in the form of extrudate of 3 mm diameter and 10 mm length and which contains 0.5% by weight of palladium, 0.2% by weight of zinc and 0.1% by weight of cadmium on alumina as the carrier is introduced into a tubular reactor having a capacity of one liter, corresponding to 1,000 parts by volume, and is heated to 220° C. Per hour, a gaseous mixture consisting of 200,000 parts by volume of ammonia and 200,000 parts by volume of hydrogen and, in co-current therewith, 50 parts of 2,6-dimethylcyclohexanol in gaseous form, are passed over this catalyst bed under atmospheric pressure. The reaction product is cooled as soon as it leaves the reactor. According to analysis by gas chromatography, the product consists of 1.3% by weight of m-xylene, 2.6% by weight of 2,6-dimethylcyclohexylamine and 96.1% by weight of 2,6-dimethylaniline. The 2,6-dimethylaniline is purified by simple distillation; boiling point 216° C. at atmospheric pressure. 100 parts of 2,6-dimethylcyclohexanol give 89.5 parts of 2,6-dimethylaniline corresponding to a yield of 94.5%.

EXAMPLE 15

Following the procedure described in Example 14, 50 parts of 2,3,6-trimethylcyclohexanol per hour are reacted at 240° C., but otherwise under the conditions of Example 14. 2,3,6-Trimethylaniline, boiling point 119° C./20 mm Hg, is obtained in a yield of 92%.

EXAMPLE 16

The procedure followed is as described in Example 14, but using α-tetralol (1,2,3,4-tetrahydro-1-naphthol) as the starting material. α-Naphthylamine, melting point 49° C., is obtained in a yield of 94%.

EXAMPLE 17

The procedure followed is as described in Example 14, but using a catalyst containing 0.5% by weight of palladium on a zinc-aluminum spinel. Under these conditions, 2,6-dimethylcyclohexanol gives a 96% yield of 2,6-dimethylaniline.

EXAMPLE 18

1,000 parts by volume of catalyst are introduced into a fluidised bed reactor having a capacity of 1.2 liters, corresponding to 1,200 parts by volume. The catalyst consists of 0.5% by weight of palladium and 0.2% by weight of zinc on $Al_2O_3$ and has a particle size of 0.2 to 0.6 mm. The temperature in the reactor is set to 220° C. and, per hour, a correspondingly preheated mixture of 200,000 parts by volume of ammonia and 200,000 parts by volume of hydrogen is introduced. 50 parts of a mixture consisting of 80% by weight of 2,6-dimethylcyclohexanol and 20% by weight of 2,6-dimethylcyclohexanone is passed continuously, per hour, through the fluidised catalyst bed thus produced. The reaction product is isolated by cooling the exit gases, and is distilled. 100 parts of 2,6-dimethylcyclohexanol/2,6-dimethylcyclohexanone mixture employed give 92 parts of 2,6-dimethylaniline. Yield: 96.5%.

EXAMPLE 19

The procedure followed is as described in Example 18, but using 3-tert.-butyl-cyclohexanol as the starting material. m-tert.-Butylaniline, boiling point 72°–73° C./0.2 mm Hg, is obtained as the end product, in a yield of 94%.

EXAMPLE 20

A mixture of 51 parts of 2-ethyl-cyclohexanol, 41 parts of ammonia and 5 parts of a fine catalyst powder containing 10% by weight of palladium and 0.2% by weight of zinc on $Al_2O_3$ is heated for 10 hours at 275° C. in a stirred autoclave having a capacity of 300 parts by volume. The autogenous pressure assumes a value of about 200 bar. The mixture is then allowed to cool and is filtered and purified by distillation. 22 parts of 2-ethylaniline, boiling point 209° C. at atmospheric pressure, and 25 parts of a mixture of 2-ethylcyclohexanol and 2-ethylcyclohexylamine are obtained. Since the latter mixture can also be converted to 2-ethylaniline, for example by proceeding as described in Example 1 or 5, the selectivity of the reaction is 95%.

EXAMPLE 21

The procedure followed is as described in Example 21, but using 2,6-dimethyl-3-(p-methylphenyl)-cyclohexanol as the starting material. 2,6-Dimethyl-3-(p-methylphenyl)-aniline, boiling point 132° C./02. mm Hg, is obtained with a selectivity of 91%.

EXAMPLE 22

The procedure followed is as described in Example 21, but using 2,6-dimethyl-3-(p-methoxyphenyl)-cyclohexanol as the starting material. 2,6-Dimethyl-3-(p-methoxyphenyl)-aniline, boiling point 151° C./0.3 mm Hg, is obtained with a selectivity of 85%.

COMPARATIVE EXPERIMENT

The procedure followed is as described in Example 14, but the catalyst used contains 0.5% by weight of palladium on alumina, without any additives. According to analysis by gas chromatography, the reaction product obtained with this catalyst has the following composition: 5% by weight of m-xylene, 11% by weight of 2,6-dimethylcyclohexanol, 8% by weight of 2,6-dimethylphenol and 76% by weight of 2,6-dimethylaniline.

We claim:

1. A process for the production of an aromatic amine having the general formula

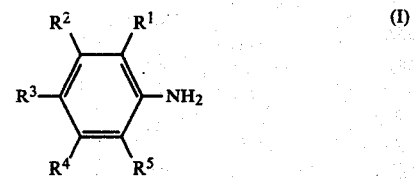

wherein at least one of $R^1$, $R^2$, $R^3$, $R^4$ and $R^5$ is different from hydrogen and may be a $C_1$ to $C_{20}$ alkyl, cycloalkyl or alkoxy group, a substituted or unsubstituted aryl or alkylaryl group, by reacting a saturated or olefinically unsaturated cyclic alcohol or ketone of the general formula

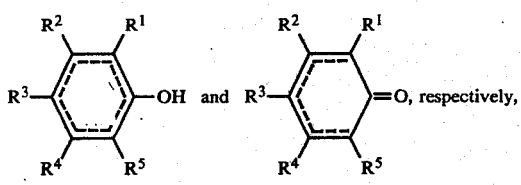

$R^1$ to $R^5$ having the aforementioned meanings, with ammonia in the presence of a (de)hydrogenating catalyst and preferably hydrogen, wherein the (de)hydrogenating catalyst is palladium and zinc and/or cadmium.

2. A process as claimed in claim 1, wherein the reaction temperature is from 100° to 350° C.

3. A process as claimed in claim 1 or 2, wherein the reaction pressure is from atmospheric pressure up to 300 bars.

4. A process as claimed in claim 3, wherein the reaction pressure is atmospheric and the reaction mixture is gaseous.

5. A process as claimed in claim 3, wherein the reaction mixture is essentially liquid.

6. A process as claimed in claim 1, wherein the ketone is olefinically unsaturated and the saturated ketone is isolated as an intermediate product.

7. A process as claimed in claim 1, wherein the palladium catalyst is deposited on a carrier selected from the group consisting of aluminum oxide, silica, a silicate of aluminum or magnesium, and carbon.

8. A process as claimed in claim 7, wherein the catalyst contains, based on the weight of the carrier, from 0.05 to 15% palladium and 0.01 to 5% zinc and/or cadmium, the carrier being aluminum oxide.

* * * * *